(12) United States Patent
Shieh et al.

(10) Patent No.: US 8,679,542 B2
(45) Date of Patent: Mar. 25, 2014

(54) CLEAVAGE KIT, AND GENE THERAPY BY USING THE SAME AND NUCLEIC ACID CLEAVAGE DETECTION APPARATUS

(75) Inventors: Dar-Bin Shieh, Tainan (TW); Tsung-Lin Tsai, Tainan County (TW); Wu-Chou Su, Tainan (TW); Kao-Shu Chuang, Kaohsiung County (TW); Jih-Ru Hwu, Hsinchu (TW)

(73) Assignee: National Cheng Kung University, Tainan (TW)

( * ) Notice: Subject to any disclaimer, the term of this patent is extended or adjusted under 35 U.S.C. 154(b) by 245 days.

(21) Appl. No.: 12/782,170

(22) Filed: May 18, 2010

(65) Prior Publication Data
US 2011/0014293 A1 Jan. 20, 2011

(30) Foreign Application Priority Data

Jul. 14, 2009 (TW) ............................... 98123812 A
Jul. 14, 2009 (TW) ............................... 98123816 A

(51) Int. Cl.
*A61K 48/00* (2006.01)
*C12M 1/34* (2006.01)
*A61P 43/00* (2006.01)
*A61K 9/00* (2006.01)
*G01N 27/26* (2006.01)

(52) U.S. Cl.
USPC ....... 424/489; 514/44 R; 435/287.2; 424/400; 204/600; 977/773; 977/906

(58) Field of Classification Search
None
See application file for complete search history.

(56) References Cited

U.S. PATENT DOCUMENTS 6,150,102 A * 11/2000 Mills et al. .................. 435/6.16

OTHER PUBLICATIONS

Tsai et al (Nanotechnology, 2008. NANO '08. 8th IEEE Conference on Aug. 18-21, 2008; p. 880-881).*
Murphy et al. (Nucleic Acids Research, 2004; 32(7): e65, pp. 1-7).*
Amiri et al. (J. Mol. Biol. 2005; 351: 776-783).*
McBain et al. (International Journal of Nanomedicine. 2008; 3(2): 169-180).*
Lytton-Jean et al (Anal. Chem. 2007; 79: 6037-6041).*
Francois et al., "Sequence-specific recognition and cleavage of duplex DNA via triple-heix formation by oligonucleotides covalently linked to a phenanthroline-copper chelate,". Proc. Natl. Acad. Sci., Dec. 1989, vol. 86, pp. 9702-9706.
Hsu et al., "Novel Arylhydrazone-Conjugated Gold Nanoparticles with DNA-Cleaving Ability: The First DNA-Nicking Nanomaterial," Bioconjugate Chem., 2007, vol. 18, pp. 1709-1712.
Tsung-Lin Tsai et al., "Photoactive Compound-Triplex-Forming Oilgonucleotide Linked Gold Nanoparticle as an Artificial Gene Specific DNA Cleaver Assembly," Nanotechnology, NANO' 08, 8th IEEE Conference, 2008, pp. 880-881.

\* cited by examiner

*Primary Examiner* — Scott Long
(74) *Attorney, Agent, or Firm* — Muncy, Geissler, Olds & Lowe, P.C.

(57) ABSTRACT

A nucleic acid cleavage kit is used to cleave a target nucleic acid. The nucleic acid cleavage kit includes a carrier, an oligonucleotide, and a nucleic acid cleavage agent. The oligonucleotide recognizes at least partial sequence of the target nucleic acid. Then, the nucleic acid cleavage agent cleaves the target nucleic acid. A nucleic acid cleavage detection apparatus including the nucleic acid cleaving kit and a gene therapy by administering the nucleic acid cleavage kit are also disclosed.

1 Claim, 13 Drawing Sheets

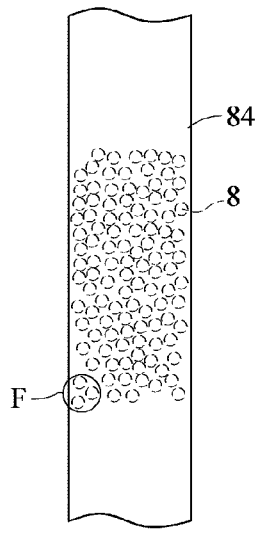 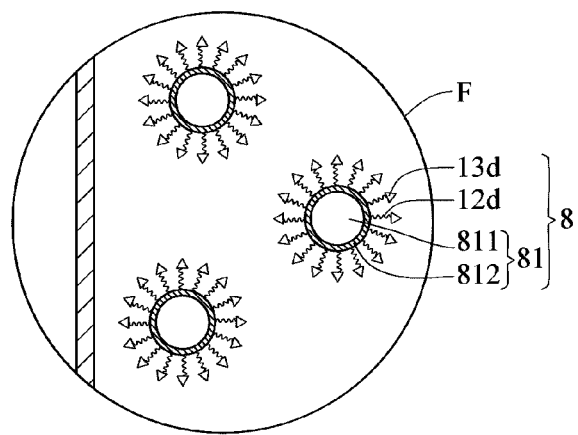
FIG. 8a  FIG. 8b
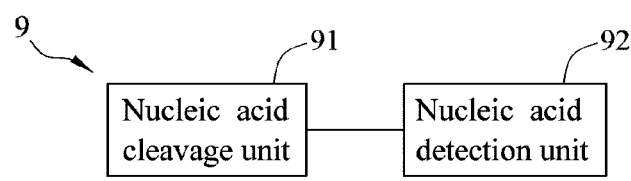
FIG. 9

SEQ ID NO:1

E primer used in the Experiment 2

1 CCTACGGCGT GCAGTGCTTC AGC

SEQ ID NO:2

E primer used in the Experiment 2

1 CGGCGAGCTG CACGCTGCCG TCCTC

SEQ ID NO:3

T primer used in the Experiment 2

1 TACCGGACTC AGATCTCGAG CTCA

SEQ ID NO:4

Primer used in the Experiment 4

1 AGCGAGTCAG TGAGCGAGGA

FIG. 15

CLEAVAGE KIT, AND GENE THERAPY BY USING THE SAME AND NUCLEIC ACID CLEAVAGE DETECTION APPARATUS

CROSS REFERENCE TO RELATED APPLICATIONS

This Non-provisional application claims priority under 35 U.S.C. §119(a) on Patent Application No(s). 098123812 and 098123816 filed in Taiwan, Republic of China both on Jul. 14, 2009, the entire contents of which are hereby incorporated by reference.

BACKGROUND OF THE INVENTION

1. Field of Invention

The present invention relates a kit and a cleavage detection apparatus, and, in particular, a kit and a cleavage detection apparatus with high sequence specificity. The present invention also relates a gene therapy by using the nucleic acid cleavage kit.

2. Related Art

Nucleic acid cleavage is a reaction of breakage in the nucleic acid sequence imposed by external force. It can be applied to clinical healthcare, biotechnology or other related fields. Previously, various types of conventional nucleic acid cleavage tools have been used. Although they may be slightly different in composition, restriction enzymes with high specificity have been widely used in recognition and cleavage on nucleic acids.

However, as the expansion of the application scope of nucleic acid cleavage, the sequence-specificity provided by restriction enzymes has been insufficient to meet the demand. For example, several important researches and medical fields, such as gene transformation, genetic mapping and gene therapy, are fairly expecting the development of a highly specific nucleic acid cleavage tool.

In particular, the lengths of the nucleic acid sequences in higher organisms like human beings are approximately 105-107 base pairs. To create a site-specific cleavage on these nucleic acids, it has to use a cleavage tool possessing the ability of recognizing at least 8 to 15 base pairs. However, conventional restriction enzymes cannot recognize more than 8 base pairs and are incompetent for nucleic acid cleavage. Similarly, for implementing a genetic analysis on a genome (generally about 105-107 base pairs in length) or nucleic acids with high sequence similarity (for example heterochromatin), the basic demand of the sequence-specific recognition ability provided by a nucleic acid cleavage tool should be more than 8 base pairs correspondingly. The conventional nucleic acid cleavage tools used restriction enzymes as the functional components are certainly insufficient for certain application.

Besides, in order to improve the ability of nucleic acid sequence recognition, conventional methods have indicated oligonucleotides, which can bind to other nucleic acid segments containing corresponding sequences, can provide highly sequence-specific recognition for particular nucleic acid sequences. However, certain feature of the oligonucleotides was only applied as a nucleic acid probe for detecting whether particular sequences exist in an organism but not applied in cooperating with nucleic acid cleavage technique.

Therefore, it is an important subject of the invention to provide a nucleic acid cleavage tool with high sequence-specificity.

SUMMARY OF THE INVENTION

In view of foregoing, the present invention is to provide a nucleic acid cleavage tool with high sequence-specificity, a method for gene therapy by using the same and a nucleic acid cleavage detection apparatus.

To achieve the above, a nucleic acid cleavage kit in accordance with the present invention includes a carrier, an oligonucleotide and a nucleic acid cleavage agent. The nucleic acid cleavage kit functions on a target nucleic acid. The first end of the oligonucleotide is bound with the carrier to recognize at least partial sequence of the target nucleic acid. The nucleic acid cleavage agent is bound to the second end of the oligonucleotide to cleave the target nucleic acid.

In one embodiment of the present invention, the nucleic acid cleavage kit is applied to a gene therapy.

In one embodiment of the present invention, the target nucleic acid is an in vitro nucleic acid.

In one embodiment of the present invention, the carrier is a nanoparticle.

In one embodiment of the present invention, the carrier includes a base and a bonding layer. The bonding layer is at least disposed on a partial surface of the base, and the first end of the oligonucleotide is bound to the bonding layer of the carrier.

In one embodiment of the present invention, the base is a flat substrate, a microplate, a spherical particle, a columnar container, a box-shaped container, a plate-shaped container or a cylindrical container.

In one embodiment of the present invention, the target nucleic acid is a single-strand nucleic acid and the oligonucleotide recognizes the target nucleic acid by forming a double helix with the partial sequence of the target nucleic acid.

In one embodiment of the present invention, the target nucleic acid is a double-strand nucleic acid and the oligonucleotide recognizes the target nucleic acid by forming a triple helix with the partial sequence of the target nucleic acid.

In one embodiment of the present invention, the oligonucleotide is a 10-mer to 30-mer oligonucleotide.

In one embodiment of the present invention, the oligonucleotide substantially consists of polypurines or modified polypurines and the partial sequence of the target nucleic acid substantially consists of polypyrimidines.

In one embodiment of the present invention, the oligonucleotide substantially consists of polypyrimidines or modified polypyrimidines and the partial sequence of the target nucleic acid substantially consists of polypurines.

In one embodiment of the present invention, the nucleic acid cleavage agent is a photoactivated nucleic acid cleavage agent.

To achieve the above, a nucleic acid cleavage detection apparatus includes the aforementioned a nucleic acid cleavage kit and a nucleic acid detection kit. The nucleic acid cleavage detection apparatus functions on a target nucleic acid. The nucleic acid detection kit detects at least one nucleic acid fragment derived from the nucleic acid after the cleavage of the nucleic acid cleavage kit.

In one embodiment of the present invention, the nucleic acid detection kit is an electrophoresis device or a nucleic acid amplification device.

To achieve the above, a method for gene therapy in accordance with the present invention includes administrating to a subject an effective amount of a nucleic acid cleavage composition to cleave a target nucleic acid. The nucleic acid cleavage composition includes a nanoparticle, an oligonucleotide and a nucleic acid cleavage agent. The first end of the oligonucleotide is bound with the nanoparticle to recognize at least partial sequence of the target nucleic acid, and the nucleic acid cleavage agent is bound to the second end of the oligonucleotide to cleave the target nucleic acid.

In one embodiment of the present invention, the target nucleic acid is a single-strand nucleic acid, and the oligonucleotide recognizes the target nucleic acid by forming a double helix with the partial sequence of the target nucleic acid.

In one embodiment of the present invention, the target nucleic acid is a double-strand nucleic acid, and the oligonucleotide recognizes the target nucleic acid by forming a triple helix with the partial sequence of the target nucleic acid.

In one embodiment of the present invention, the oligonucleotide is a 10-mer to 30-mer oligonucleotide.

In one embodiment of the present invention, the oligonucleotide substantially consists of polypurines or modified polypurines, and the partial sequence of the target nucleic acid substantially consists of polypyrimidines.

In one embodiment of the present invention, the oligonucleotide substantially consists of polypyrimidines or modified polypyrimidines and the partial sequence of the target nucleic acid substantially consists of polypurines.

In one embodiment of the present invention, the nucleic acid cleavage agent is a photoactivated nucleic acid cleavage agent.

In summary, the nucleic acid cleavage kit, the method for gene therapy by using the same and the nucleic acid cleavage detection apparatus in accordance with the present invention specifically recognize the partial sequence of the target nucleic acid by the oligonucleotide and thereby cleave the target nucleic acid by the nucleic acid cleavage agent. Because the oligonucleotide can recognize longer sequence, the nucleic acid cleavage kit can perform its cleavage function with high sequence specificity for nucleic acid in vivo and in vitro. Comparing to prior art, the present invention provides a novel nucleic acid cleavage kit and a method for gene therapy by using the same to overcome the issue that the application scope of nucleic acid cleavage is limited by the insufficient recognition ability of restriction enzymes. It is beneficial for achieving the goal of clinical application and reducing side effects. In addition, the present invention also provides a novel nucleic acid cleavage tool for in vitro usage, which can recognize longer sequence and be easily modified and manufactured such that it expands the application scope of nucleic acid cleavage and reduces production cost.

BRIEF DESCRIPTION OF THE DRAWINGS

The invention will become more fully understood from the detailed description and accompanying drawings, which are given for illustration only, and thus are not limitative of the present invention, and wherein:

FIG. 7b is a cross-sectional figure along the section line E shown in FIG. 7a;

FIG. 8a is a schematic figure of the nucleic acid cleavage kit filled in a column in accordance with the fourth embodiment of the present invention;

FIG. 8b is a partial enlarged figure of the region F shown in FIG. 8a;

FIG. 9 is a block diagram of the nucleic acid cleavage detection apparatus in accordance with the embodiment of the present invention;

FIG. 15 is a sequencing list indicating the relative information of the primer used in the present invention.

DETAILED DESCRIPTION OF THE INVENTION

Figure 1:
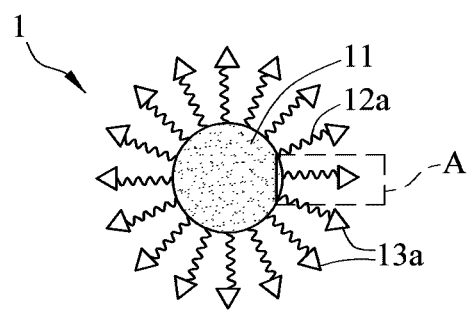
FIG. 1 is a schematic figure of the nucleic acid cleavage kit in accordance with the first embodiment of the present invention.

The terms "recognition" or "recognize" as used herein is a characteristic that one nucleic acid can distinguish a target nucleic acid from others by forming of base-pairings (bps) to combine the nucleic acid and the target nucleic acid into one. Because the formation of base-pairings depends on whether two nucleic acids can form chemical bonds between the nitrogenous bases of their nucleotides at the corresponding positions, a candidate nucleic acid without a complementary sequence cannot complete the aforementioned base-paring process. The term "cleavage" or "cleave" as used herein is to generate at least one gap or nick on a continuous nucleotide sequence. As for function, the cleavage reaction can result in the loss function of an original gene containing the continuous nucleotide sequence.

The nucleic acid cleavage kit in accordance with the present invention can provide a cleavage reaction with high sequence specificity for particular nucleic acids. The application field of the nucleic acid cleavage kit is for example but not limited to gene therapy or sequence recombination.

In one embodiment of the present invention, the nucleic acid cleavage kit is applied to gene therapy. Meanwhile, the target nucleic acid is an in vivo target nucleic acid. The target nucleic acid can be for example but not limited to a whole genome or a part thereof, an artificial or synthetic nucleic aid, the aforementioned nucleic acid with modification or a natural or synthetic nucleoid. In addition, the target nucleic acid for the nucleic acid cleavage kit also can be an in vitro target nucleic acid including a whole genome or a part thereof purified from an organism, a natural nucleic acid purified from a cell, a synthetic nucleic acid, the aforementioned nucleic acid with modification, or a natural or synthetic nucleoid.

The target nucleic acid further can be a nucleic acid unit with a biological function such as a gene, a gene fragment or a promoter, a enhancer or a poly(A) tail of a gene. In one embodiment of the present invention, the nucleic acid can be a nucleic acid unit of the double-stranded deoxyoligonucleotide chain with a biological function. The aforementioned gene with a biological function can express a polypeptide or a protein directly or indirectly involved in a pathogenic mechanism of a genetic disease or gene mutation. The genetic disease can be for example but not limited to leukemia, diabetes, Huntington's disease, and the gene mutation is considered to induce various cancers.

However, to be noted, if the target nucleic acid is the aforementioned nucleic acid unit with a biological function, the length of the target nucleic acid may include certain sequence of the nucleic acid unit with biological function and the adjacent sequences. It is to provide enough binding length for the oligonucleotide so as to prevent miscleavage from occurring.

First Embodiment

The following and accompanying figures describe the nucleic acid cleavage kit in accordance with the first embodiment of the present invention.

Figure 2:
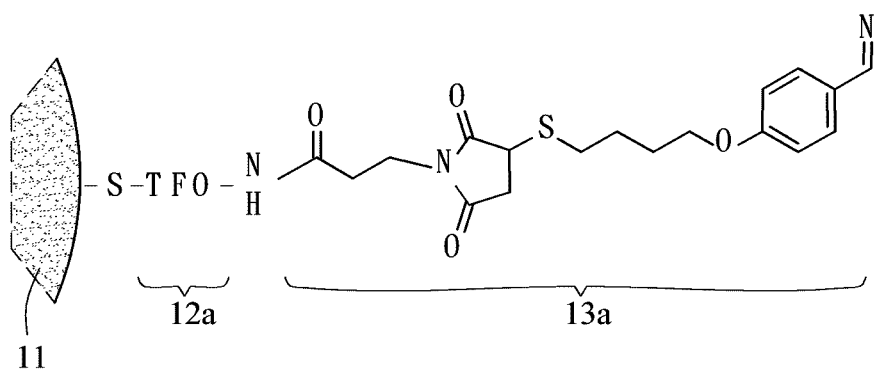
FIG. 2 is a partial enlarged figure of the region A shown in FIG. 1.

FIG. 1 is a cross-sectional figure of the nucleic acid cleavage kit in accordance with the present invention, and FIG. 2 is the partial enlarged figure of FIG. 1. As shown in FIG. 1 and FIG. 2, the nucleic acid cleavage kit 1 in accordance with the first embodiment of the present invention includes a carrier 11, an oligonucleotide 12a and a nucleic acid cleavage agent 13a. The nucleic acid cleavage kit 1 functions on a target nucleic acid (not shown in the figure). The first end of the oligonucleotide 12a is bound with the carrier 11 to recognize at least partial sequence of the target nucleic acid. The nucleic acid cleavage 13a agent is bound to the second end of the oligonucleotide 12a to cleave the target nucleic acid.

In the present invention, the carrier 11 is a nanoparticle. In more detailed, the carriers 11 can be nanoparticles with uniform size, shape and/or chemical composition or nanoparticles with different size, shape and/or chemical composition. To be noted, when the carrier 11 is a nanoparticle, the nucleic acid cleavage kit 1 can be considered as a sort of nucleic acid cleavage compositions, in particular for medical use.

The aforementioned nanoparticle can be for example but not limited to an aggregate particle, an isotropic nanoparticle such as a solid spheral nanoparticle or a hollow spheral nanoparticle, an anti-isotropic nanoparticle such as an anisotropic conical, rectangular or rhombic nanoparticle, a dendrimer or a composite nanoparticle such as a core-shell nanoparticle. In the present embodiment, the carrier 11 is a solid spheral nanoparticle.

In addition, when the carrier 11 is a nanoparticle, the mean particle diameter of the carrier 11 is about 1 to 100 nanometers. In the present embodiment, the mean particle diameter of the carrier 11 is about 10 to 30 nanometers.

Similarly, when the carrier 11 is a nanoparticle, the material of the carrier 11 can include metal and/or magnetic material. The metal can be for example Au, Ag, Pd, Pt, Ni, Al, In, Ti, Cu, Fe, Co, Zn, Sn, Cr and other metal easily to form into spherical shape. The magnetic material is substantially material with paramagnatism and thereby can be attracted or repulsed by an external magnetic force, for example ferrous oxide or nickel oxide. It benefits the operation and recycling of the nucleic acid cleavage kit 1. In the present embodiment, the carrier 11 is a gold nanoparticle, which has the features of good biocompatibility and in vitro stability.

The material of the aforementioned nanoparticle can also include semiconductor or inorganic material. The semiconductor can be cadmium selenide, cadmium sulfide, or zinc sulfide-coated cadmium selenide or cadmium sulfide. In addition, the inorganic material can be silicon or silicon dioxide. The organic material included in the aforementioned nanoparticle can be poly(lactide-co-glycolide) (PLGA).

The oligonucleotide 12a can be for example an oligonucleotide derived from purification, polymerase chain reaction (PCR) or chemical synthesis. The sequence of the oligonucleotide 12a is about 10 to 30 mers in length, and preferably is about 11 to 15 mers in length. As for its molecular composition, the oligonucleotide 12a can be a RNA oligonucleotide, a DNA oligonucleotide or the aforementioned oligonucleotide with modifications.

The first end of the oligonucleotide 12a is connected to the carrier 11. As shown in FIG. 1 and FIG. 2, in the present invention, the oligonucleotide 12a and the carrier 11 are connected with a covalent bond. As shown in FIG. 2, in more detailed, the 5' end of the oligonucleotide 12a includes a thiol group connected to the carrier 11 with a covalent bond. However, other connection type between the oligonucleotide 12a and the carrier 11 can be used as well, for example but not limited hydrogen bond, van der Waals' forces or static electric interaction.

In the present embodiment, the oligonucleotide 12a substantially consists of polypurines to form a triple helix structure with at least partial sequence of the target nucleic acid. The triple helix structure is called as a triplex-forming oligonucleotide (TFO). Correspondingly, the at least partial sequence of the target nucleic acid substantially consists of polypyrimidines. In contrast, in another embodiment of the present invention, the oligonucleotide 12a substantially consists of polypyrimidines and the at least partial sequence of the target nucleic acid substantially consists of polypurines.

The term "purine" as used herein substantially indicates an adenine or a guanine. However, it further includes a modified adenine or guanine or a synthesized analogue of adenine or guanine. In addition, the term "pyrimidine" as used herein substantially indicates a thymine, a cytosine or a uracil. However, it further includes a modified thymine, cytosine or uracil or a synthesized analogue of athymine, a cytosine or a uracil.

As for the modification, the major modification sites of the purine or pyrimidine can be classified to three portions: the nucleobase, the sugar and the phosphate backbone. The modified product or synthesized analogue can be for example but not limited to 7-deaza-2'-deoxyxanthosine, 2'-deoxy-6-thioguanosine, 5-fluoro-deoxyuracil, 2'-deoxynebularine, 5-methylcytosine, 5-propargylamino-2'-deoxyuridine, nucleotides containing 2'-methoxylated riboses, 5-propynyldeoxyuridine, nucleotides with riboses replaced by 2'-aminoethylribose and analog thereof, O2',O4'-methylene-linked nucleic acid, locked nucleic acid (LNA) monomer, O2',O4'-ethylene linked nucleic acid (ENA) monomer and peptide nucleic acid (PNA) (Please reference Chan et al., Triplex DNA: fundamentals, advances, and potential applications for gene therapy, J. Mol. Med., 75, 267-282, 1997.)

In addition, the term "triple helix" as used herein is a sort of helix structure formed by the interaction between the oligonucleotide 12a and a double-stranded target nucleic acid including the corresponding sequences, which can form chemical bonds between the nucleobases. In more detailed, the interaction occurs at the major grooves or minor grooves of the double-stranded target nucleic acid.

To be noted, the nucleic acid cleavage kit 1 in accordance with the present invention can include the carrier 11 connected by more than one sort of the oligonucleotides 12a instead of one such that it can simultaneously react with more than one sort of the target nucleic acid.

The nucleic acid cleavage agent 13a is used to cleave the target nucleic acid, and the selection of the nucleic acid cleavage agent can depend on the molecular composition of the target nucleic acid. Preferably, the nucleic acid is for example but not limited to a synthesized deoxyribonucleic acid cleavage agent.

In the present embodiment, the nucleic acid cleavage agent 13a is a photoactivated nucleic acid cleavage agent such as arylhydrazone (shown in FIG. 2). Other nucleic acid cleavage agents can be for example azidoproflavine, azidophenacyl or azido or ellipticine derivatives activated by a light source with a wavelength longer than 300 nanometers.

The second end of the oligonucleotide 12a is connected to the nucleic acid cleavage agent. As shown in FIG. 1 and FIG. 2, in the present embodiment, the oligonucleotide 12a and the nucleic acid cleavage agent 13a are connected by a covalent bond. In more detailed, as shown in FIG. 2, the 3' end of the oligonucleotide 12a includes an amino group connected to the nucleic acid cleavage agent 13a by a covalent bond.

In another aspect of the present embodiment, the first end of the oligonucleotide 12a can further be connected to the carrier 11 via a spacer. The spacer such as poly(ethylene glycol) (PEG) can adjust the water solubility of the nucleic acid cleavage kit 1.

Figure 3:
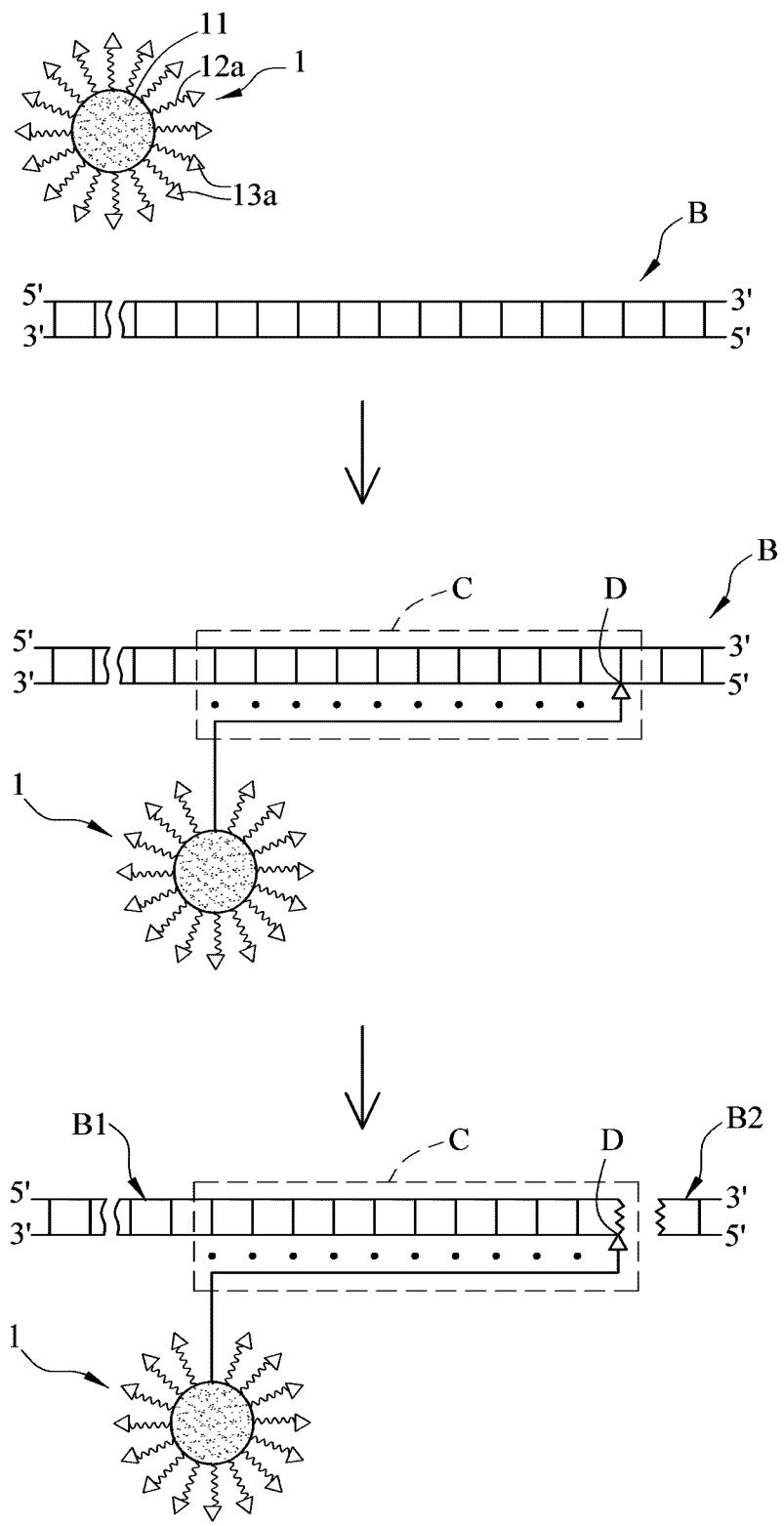
FIG. 3 is a flow chart of the cleavage process of the nucleic acid cleavage kit with high sequence specificity in accordance with the first embodiment of the present invention.

The following and accompanying FIG. 3 are taken for an example to describe the reaction mechanism of the nucleic acid cleavage kit 1 in accordance with the first embodiment.

The nucleic acid cleavage kit 1 recognizes the at least partial sequence of the target nucleic acid by the oligonucleotide 12a, and then cleaves the target nucleic acid by the nucleic acid cleavage agent 13a. As shown in FIG. 3, when the nucleic acid cleavage kit 1 functions on the target nucleic acid B, the oligonucleotide 12a recognizes the at least partial sequence of the target nucleic acid B. In addition, the structure of the target nucleic acid B is a double helix. Therefore, a triple helix structure (shown in region C) is formed by the formation of chemical bonds between the oligonucleotide 12a and the at least partial sequence of the target nucleic acid B.

If the target nucleic acid B is a single-stranded nucleic acid, the structure formed by the oligonucleotide 12a and the target nucleic acid B turns into a double helix. After the oligonucleotide 12a recognizes the target nucleic acid, the nucleic acid cleavage agent 13a functions and generates a breakage at the desired cleavage site D on the target nucleic acid B with a continuous sequence. In more detailed, the desired cleavage site D can be on base pair within or adjacent to the region C of the target nucleic acid B. In the present embodiment, the desired cleavage site D is on the base pair within the region C of the target nucleic acid B such that the nucleic acid cleavage kit 1 cleaves the target nucleic acid B into two nucleic acid fragments B1 and B2.

Second Embodiment

The following and accompanying figures describe the nucleic acid cleavage kit in accordance with the second embodiment of the present invention.

Figure 4:
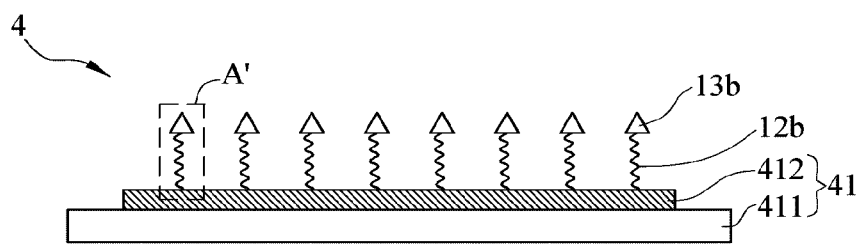
FIG. 4 is a cross-sectional figure of the nucleic acid cleavage kit in accordance with the second embodiment of the present invention.
Figure 5:
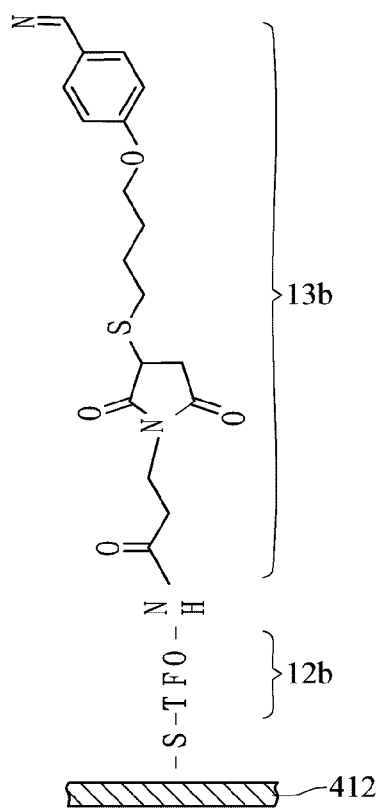
FIG. 5 is a partial enlarged figure of the region A shown in FIG. 4.

FIG. 4 is a cross-sectional figure of a nucleic acid cleavage kit in accordance with the second embodiment of the present invention, and FIG. 5 is a partial enlarged figure of the region A' of FIG. 4. As shown in FIG. 4 and FIG. 5, the nucleic acid cleavage kit 4 includes a carrier 41, an oligonucleotide 12b and a nucleic acid cleavage agent 13b. The nucleic acid cleavage kit 4 functions on a target nucleic acid. The first end of the oligonucleotide 12b is bound with the carrier 41 to recognize at least partial sequence of the target nucleic acid. The nucleic acid cleavage agent 13b is bound to the second end of the oligonucleotide 12b to cleave the target nucleic acid.

As shown in FIG. 4 and FIG. 5, in the present embodiment, the carrier 41 includes a base 411 and a bonding layer 412. The bonding layer 412 is at least disposed on a partial surface of the base 411. In more detailed, the bonding layer 412 is at least disposed on the partial surface of the base 411 by for example but not limited to coating.

The base 411 can be a flat substrate, a microplate, a spherical particle, a columnar container, a box-shaped container, a plate-shaped container, a cylindrical container or other two-dimensional/three-dimensional configurations. In the present embodiment, the base 411 is a flat substrate (shown in FIG. 5).

In addition, the material of the bonding layer 412 can include metal or magnetic material. The metal can be for example Au, Ag, Pd, Pt, Ni, Al, In, Ti, Cu, Fe, Co, Zn, Sn, Cr and other metal easily formed into flat layer-shaped. In the present embodiment, the bonding layer 412 preferably includes Au. The magnetic material substantially refers to material with paramagnetism such as ferrous oxide or nickel oxide. The bonding layer 412 can also include semiconductor or inorganic material. In the present embodiment, the semiconductor can be for example but not limited to cadmium selenide, cadmium sulfide, or zinc sulfide-coated cadmium selenide or cadmium sulfide. In addition, the inorganic material can be silicon or silicon dioxide.

The technical characteristics of the oligonucleotide 12b and the nucleic acid cleavage agent 13b are similar to those of the oligonucleotide 12a and the nucleic acid cleavage agent 13a in the first embodiment such that the detailed description thereof will be omitted.

Figure 6:
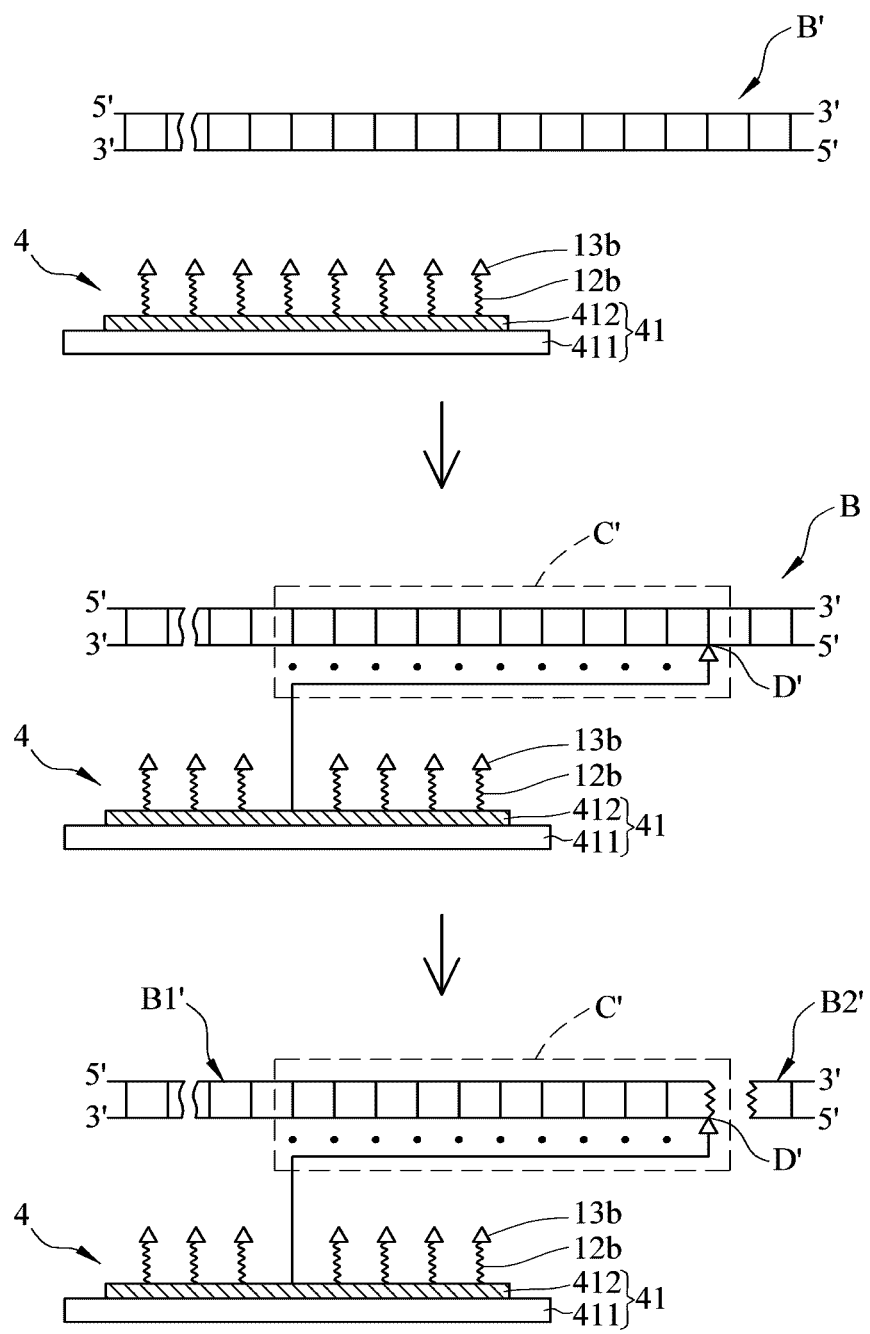
FIG. 6 is a flow chart of the cleavage process of the nucleic acid cleavage kit with high sequence specificity in accordance with the second embodiment of the present invention.

The following and accompanying FIG. 6 are taken for an example to describe the reaction mechanism of the nucleic acid cleavage kit 4 in accordance with the second embodiment of the present invention.

In the present embodiment, the nucleic acid cleavage kit 4 recognizes the at least partial sequence of the target nucleic acid by the oligonucleotide 12b, and then cleaves the target nucleic acid by the nucleic acid cleavage agent 13b. As shown in FIG. 6, when the nucleic acid cleavage kit 4 is close to the at least partial sequence of the target nucleic acid B', the oligonucleotide 12b is capable of recognizing at least partial sequence of the target nucleic acid. Because the target nucleic acid B' is a double helix, a triple helix (shown in region C') is formed by the formation of chemical bonds between the oligonucleotide 12b and the at least partial sequence of the target nucleic acid B'.

If the target nucleic acid B' is a single-stranded nucleic acid, the structure formed by the oligonucleotide 12b and the target nucleic acid B' is a double helix structure. After the oligonucleotide 12b recognizes the target nucleic acid, the nucleic acid cleavage agent 13b functions and generates a breakage at the desired cleavage site D' on the target nucleic acid B' with a continuous sequence. In more detailed, the desired cleavage site D' can be on the base pair within or adjacent to the region C' of the target nucleic acid B'. In the present embodiment, the desired cleavage site D' is on the base pair within the region C' of the target nucleic acid B' such that the nucleic acid cleavage kit 4 cleaves the target nucleic acid B into two nucleic acid fragments B1 and B2.

Furthermore, in the present embodiment, because the nucleic acid cleavage kit 4 can include a certain amount of the oligonucleotides and the nucleic acid cleavage agents, the nucleic acid cleavage kit 4 can be used for the sequence detection of large amounts of nucleic acids Third Embodiment The following and accompanying related figures are taken for an example to describe the third embodiment of the present invention.

Figure 7A:
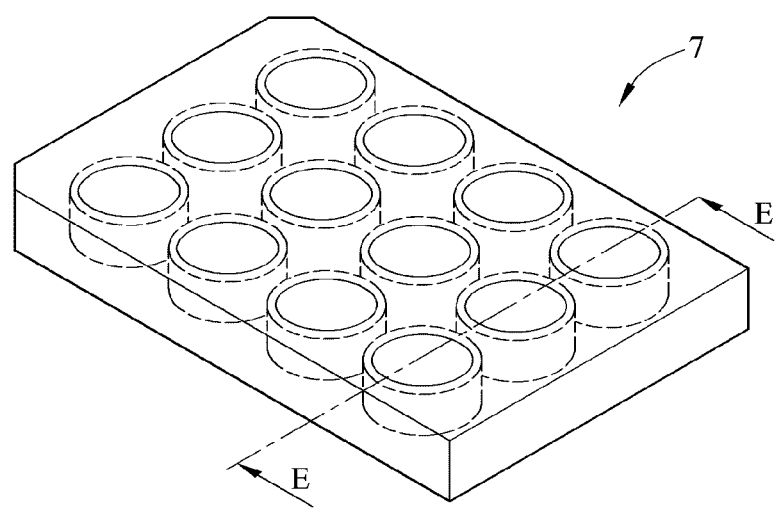
FIG. 7a is a top view of the nucleic acid cleavage kit in accordance with the third embodiment of the present invention.
Figure 7B:
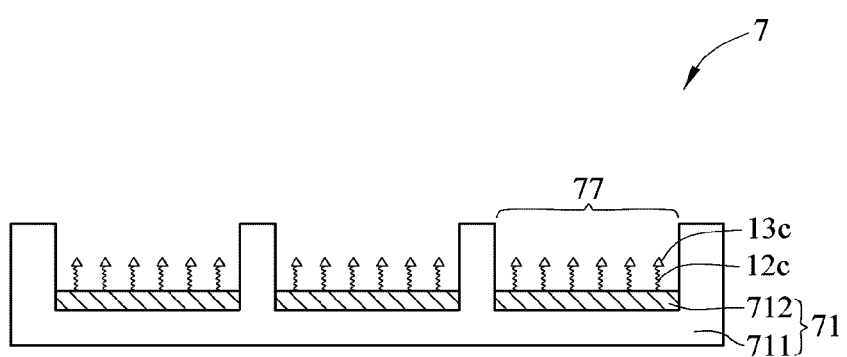

FIG. 7a is a side view of the nucleic acid cleavage kit 7 in accordance with the third embodiment of the present invention, and FIG. 7b is a cross-sectional figure along the section line E shown in FIG. 7A. As shown in FIG. 7a and FIG. 7b, the nucleic acid cleavage kit 7 includes a carrier 71, an oligonucleotide 12c and a nucleic acid cleavage agent 13c. The nucleic acid cleavage kit 7 functions on a target nucleic acid. The first end of the oligonucleotide 12c is bound with the carrier 71 to recognize at least partial sequence of the target nucleic acid. The nucleic acid cleavage agent 13c is bound to the second end of the oligonucleotide 12c to cleave the target nucleic acid.

As shown in FIG. 7b, in the present embodiment, the carrier 71 includes a base 711 and a bonding layer 712. The base 711 is a microplate such as a 12-well plate, and the bonding layer 712 is disposed on the bottom surface of each well 77 of the base 711 by for example but not limited to coating.

In the present embodiment, the technical characteristics of the nucleic acid, the bonding layer 712, the oligonucleotide 12c and the nucleic acid cleavage agent 13c are similar to those of the nucleic acid, the bonding layer 412, the oligonucleotide 12a and the nucleic acid cleavage agent 13a in the first embodiment such that the detailed description thereof will be omitted.

In addition, the cleavage process of the nucleic acid cleavage kit 7 in the present embodiment to the target nucleic acid is similar to the cleavage process of the nucleic acid cleavage kit 4 shown in FIG. 6 such that the detailed description thereof will be omitted. To be noted, because the nucleic acid cleavage kit 7 includes 12 separated wells 77 (shown in FIG. 7a), each of the wells 77 can independently can be bound with the same or different oligonucleotides 12c and the nucleic acid cleavage agents 13c after the bonding layer 712 is disposed on the bottom surface of each of the wells 77 of the base 711.

Fourth Embodiment

The following and accompanying FIG. 8 are taken for an example to describe the fourth embodiment of the present embodiment.

FIG. 8a is a schematic figure of a nucleic acid cleavage kit 8 in accordance with the fourth embodiment of the present invention, and FIG. 8b is a partial enlarged figure of the region F shown in FIG. 8a. To be noted, the nucleic acid cleavage kit 8 is filled in a column 84. As shown in FIG. 8a and FIG. 8b, the nucleic acid cleavage kit 8 includes a carrier 81, an oligonucleotide 12d and a nucleic acid cleavage agent 13d. The nucleic acid cleavage kit 8 functions on a target nucleic acid. The first end of the oligonucleotide 12d is bound with the carrier 81 to recognize at least partial sequence of the target nucleic acid. The nucleic acid cleavage agent 13d is bound to the second end of the oligonucleotide 12d to cleave the target nucleic acid.

As shown in FIG. 8a, a chromatographic column 84 is filled with the nucleic acid cleavage kit 8 in accordance with the present embodiment. In addition, as shown in FIG. 8b, the carrier 81 includes a base 811 and a bonding layer 812. The base 811 is a spheroid particle, and the bonding layer 812 is disposed on the surface of the base 811 by for example but not limited to coating.

In the present embodiment, the technical characteristics of the target nucleic acid, the bonding layer 812, the oligonucleotide 12d and the nucleic acid cleavage agent 13d are similar to those of the aforementioned target nucleic acid, bonding layer 412, oligonucleotide 12b and nucleic acid cleavage agent 13b such that the detailed description thereof will be omitted.

Similarly, the cleavage process of the nucleic acid cleavage kit 8 in accordance with the present embodiment to the target nucleic acid is similar to the cleavage process of the nucleic acid cleavage kit 4 shown in FIG. 6 such that the detailed description thereof will be omitted. As shown in FIG. 8a, because the chromatographic column 84 can be filled with the nucleic acid cleavage kits 8 with the same or different oligonucleotides 12d in any proportion, it can provide large amounts of nucleic acid the sequence detection for at least one sort of target nucleic acids specifically.

The nucleic acid cleavage kit 1 in accordance with the present invention also can be further processed into a pharmaceutical composition. In the first embodiment, the nucleic acid cleavage kit 1 can further include at least one acceptable pharmaceutical carrier, for example but not limited to microcrystalline cellulose, mannitol, glucose, dried skim milk, starch, polyvinylprrolidone or a combination thereof.

In addition, the nucleic acid cleavage kit 1 in the pharmaceutical composition form can be administered to a subject in need for example but limited to orally, parentally, by inhalation spray, topically, nasally or via an implanted reservoir, microinjection or a gene gun. In more detailed, the term "parenteral" as used herein includes subcutaneous, intracutaneous, intravenous, intramuscular, intraarticular, intraarterial, intrasynovial or infrasternal injection or infusion techniques.

In summary, because the nucleic acid cleavage kit in accordance with the present invention can recognize the at least partial sequence of the target nucleic acid by the oligonucleotide and then cleave the target nucleic acid by the nucleic acid cleavage agent, it can provide cleavage reaction to the target nucleic acid with high sequence specificity by recognizing more than 10 nucleotide units in operation. In gene therapy, it can prevent the generation of undesired cleavage to affect the quality of healthcare or induce side effects. Furthermore, a large amount of the oligonucleotides and the nucleic acid cleavage agent can be connected to the carrier to provide sufficient cleavage reactions in a use, and thereby the nucleic acid cleavage kit in accordance with the present invention is suitable for treating a large amount of nucleic acids. In addition, since the carrier can be a nanoparticle, it helps users to deliver the nucleic acid cleavage kit to a target site or recycle the nucleic acid cleavage kit from human body efficiently, and can further combine with image technique to track the nucleic acid cleavage kit.

The nucleic acid cleavage kit of the present invention can be applied to cleave nucleic acids in vitro for preventing the generation of undesired fragments derived from the nucleic acids from affecting consequential analysis as well. The use of nucleic acid cleavage agents produced from general chemical synthesis can reduce the production cost for cleaving target nucleic acids and is more convenient for cleavage and detection. Moreover, the nucleic acid cleavage kit is flexible for application resulting from various sorts and modification sites of the chemical synthesized nucleic acid cleavage agents.

The oligonucleotide of the nucleic acid cleavage kit in accordance with the present invention can further be customized depending on target nucleic acids. In addition, the manufacturing process of the nucleic acid cleavage kit is simple such that it contributes to the expansion of nucleic acid cleavage market.

The following and accompanying related figures are taken for an example to describe a nucleic acid cleavage detection apparatus in accordance one embodiment of the present invention.

As shown in FIG. 9, the nucleic acid cleavage detection device 9 in accordance the present invention functions on a target nucleic acid, and it includes a nucleic acid cleavage kit 91 and a nucleic acid detection kit 92. The nucleic acid cleavage kit 91 includes a carrier, a oligonucleotide, and a nucleic acid cleavage agent. The first end of the oligonucleotide is bound with the carrier to recognize at least partial sequence of the target nucleic acid, and the nucleic acid cleavage agent is bound with a second end of the oligonucleotide to cleave the target nucleic acid. Because the nucleic acid cleavage kit 91 and the elements thereof are similar to the aforementioned nucleic acid cleavage kit 1 and the elements thereof, the detail description will be omitted.

The nucleic acid detection kit 92 detects at least one nucleic acid fragment derived from the nucleic acid after the cleavage of the nucleic acid cleavage kit 91. The detection assay provided by the nucleic acid detection kit 92 can be set up by applying a physical and/or chemical factor to the nucleic acid fragment to observe the result of the nucleic acid fragment response to the physical and/or chemical factor in accordance with the length of the nucleic acid fragment. To be noted, the nucleic acid detection kit 92 is for example but not limited to an electrophoresis device or a nucleic acid amplification device.

Accordingly, the nucleic acid cleavage detection device in accordance with the present invention can provide cleavage reaction with high sequence specificity and further detect the at least one nucleic acid fragment after the cleavage of the nucleic acid cleavage kit. It can collects detection data directly and thereby validate real-time results.

The following takes the first embodiment of the present invention for an example to describe a method for gene therapy by administering the nucleic acid cleavage kit.

The method for gene therapy in accordance with the first embodiment includes administering to a subject in need an effective amount of a nucleic acid cleavage composition to cleave a target nucleic acid. The nucleic acid cleavage composition includes a nanoparticle, an oligonucleotide and a nucleic acid cleavage agent. The first end of the oligonucleotide is bound with the nanoparticle to recognize at least partial sequence of the target nucleic acid and the nucleic acid cleavage agent is bound to the second end of the oligonucleotide to cleave the target nucleic acid. Because the aforementioned nucleic acid cleavage composition and the elements thereof are similar to the nucleic acid cleavage kit and the elements thereof disclosed in the present invention, the detailed description will be omitted.

The term "subject in need" used herein includes a subject, who has a disease, or a symptom of either diseases, or a predisposition toward the disease, needs to be treated with gene therapy with the purpose to cure, heal, alleviate, relieve, alter, remedy, ameliorate, improve, or affect the disease, the symptoms of the disease, or the predisposition toward the disease.

In addition, in present embodiment, the method can be considered as an upstream step to provide cleavage reaction with high sequence specificity in gene therapy, and then combines with corresponding sequential steps to complete the entire gene therapy process for different diseases specifically. The sequential steps can be for example but not limited to inserting a normal gene, replacing a defect/mutated gene with a normal gene or suppressing/knocking out an overexpressed gene. Generally, the last step of the gene therapy process is manipulating a DNA repair mechanism to repair the breakage on the target nucleic acid and then restore the target nucleic acid as the original structure thereof.

Therefore, the method for gene therapy in accordance with the present invention can provide cleavage reaction with high sequence specificity for the target nucleic acid such that the method is able to perform gene therapy at the specific site on the target nucleic acid precisely to repair defect or mutated nucleic acid sequences. Since the method is contributive to prevent the non-specificity of gene therapy occurring on the nucleic acids in organisms, it improves the quality of healthcare and reduces side effects during the period of treatment.

The following and accompanying figures take a number of experiments for examples to describe the manufacturing method and the cleavage mechanism of the nucleic acid cleavage kits in accordance with the embodiments of the present invention.

Experiment 1: The Manufacture of the Nucleic Acid Cleavage Kit in Accordance with the First Embodiment The following takes a synthesis experiment for an example to describe the manufacturing method of the nucleic acid cleavage kit in accordance with the present invention.

Figure 10:
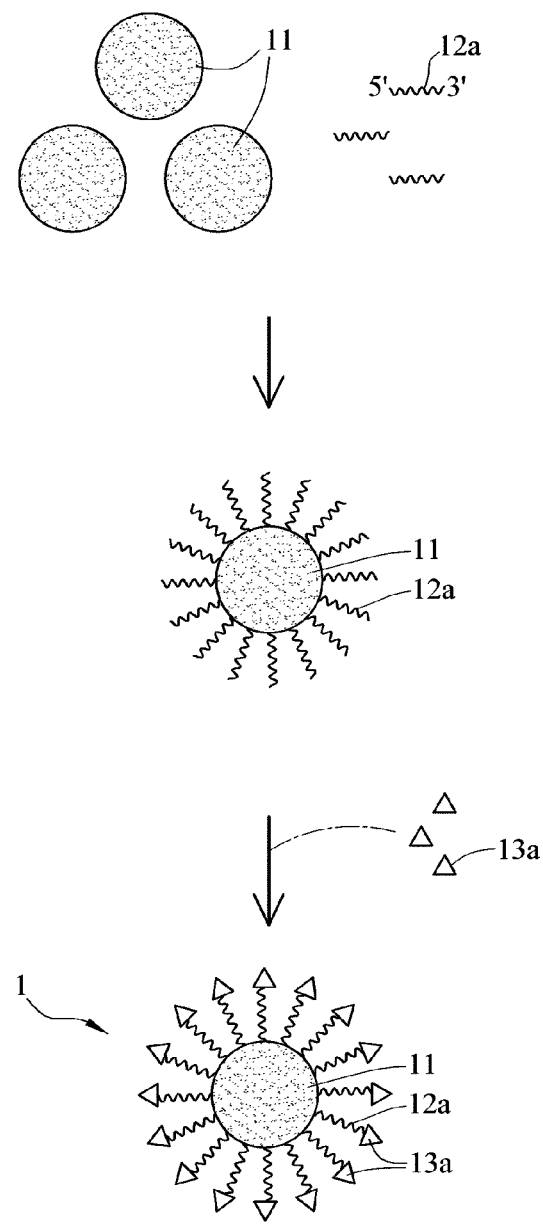
FIG. 10 is a synthesis flow chart of the nucleic acid cleavage kit in accordance with the first embodiment of the present invention.

As shown in FIG. 10, the carrier 11 (a gold nanoparticle) was provided by using sodium citrate reduction (please reference to Frens, G Controlled nucleation for the regulation of the particle size in monodisperse gold suspensions. Nat. Phys. Sci., 241, 20-22, 1973, and Grabar, et al., Preparation and characterization of Au colloid monolayers., Anal. Chem., 67, 735-743, 1995).

In the meantime, each of the oligonucleotides 12 was prepared by modifying the 5' end (the first ends) with a thiol group. The carrier 11 was incubated with the oligonucleotides 12 in the molar ratio of 1:100, and the mixture was gently shaken (<1 Hz) at 4° C. with 10 mM phosphate buffers for 24 hrs. on an orbital shaker and then processed through a gradient of salt concentration (0.3M NaCl/10 mM phosphate buffer) to connect the oligonucleotides 12 to the carrier 11 by forming covalent bonds on the thiol groups.

The nucleic acid cleavage agents 13 were provided to connect to the 3' ends (the second ends) of the oligonucleotides 12. The 3' ends of the oligonucleotides 12 were modified with amino groups in advance, and the nucleic acid cleavage agents 13 were N-(β-maleimidopropyloxy)-succinimide ester hydrazones (BMPSs) compounds. The carrier 11 connected with the oligonucleotides 12 was mixed with the nucleic acid cleavage agents 13 at room temperature for 2 hrs. The carrier 11 was incubated with the nucleic acid cleavage agents 13 in the molar ratio of 1:100, and thereby formed the nucleic acid cleavage kit 1. The nucleic acid cleavage kit 1 was resuspended with phosphate buffer and then stored at 4° C. in the dark for further use.

Experiment 2: The in vivo Cleavage Reaction with High Sequence Specificity Generated by the Nucleic Acid Cleavage Kit in Accordance with the First Embodiment Human cervical carcinoma (HeLa) cell line is taken for an example and was established as an enhanced green fluorescent protein (EGFP) HeLa cell model (also called as 2-B2 cells in the following) for observing the in vivo cleavage reaction with high sequence specificity generated by the nucleic acid cleavage kit.

HeLa cell line was cultured with DMEM medium contained 10% fetal bovine serum (FBS) and 1% antibiotics (PSF) at 37° C. under a 5% humidified CO2 incubator. For EGFP expression, the plasmids were constructed and then transferred into HeLa cells. The two single-stranded sequences recognized by the oligonucleotide anneal with each other by decreasing the temperature to form a double-stranded insert with 5' EcoRI and 3' BamHI sequence overhangings. The double-stranded insert was then ligated with pEGFP-N1 vector (CLONTECH Laboratories, Inc.) between EcoRI and BamHI restriction site to form the plasmid, which can be recognized by the oligonucleotide and express EGFP. To be noted, the oligonucleotide was able to recognize upstream of EGFP coding sequence, and two sequences were in the same reading frame. Then, the plasmid was validated by DNA sequencing.

The vector containing the oligonucleotide recognition sequence and EGFP expression sequence was transiently transfected into the aforementioned HeLa cells incubated in a constant temperature incubator by Lipofectamine 2000 (Invitrogen) method following manufacturer's protocol. Upon the stage 60% confluent on a culture plate, HeLa cells were harvested for transfection. Then a single colony was picked from successfully transfected HeLa cells and screened by 600 ug/ml G418 (Sigma, A1720) for one month to collect desired 2-B2 cells.

The 2-B2 cells were seeded into 6-well microplate with 1×105 density then incubated for 24 hours. A nucleic acid cleavage kit was added into each well to the concentration of 0.5 uM. Waiting for 5 hours to make sure the 2-B2 cells uptake the nucleic acid cleavage kit. The 2-B2 cells are exposed in the 460 nm blue LED for 15 mins to activate the nucleic acid cleavage reaction. After the light exposure, the 2-B2 cells were cultured for 17 hours in an appropriate manner to degrade the EGFP protein originally existing in the 2-B2 cells before processing with the nucleic acid cleavage kit. Then, the result was observed by two techniques: microscopy and genomic DNA PCR.

Figure 11A:
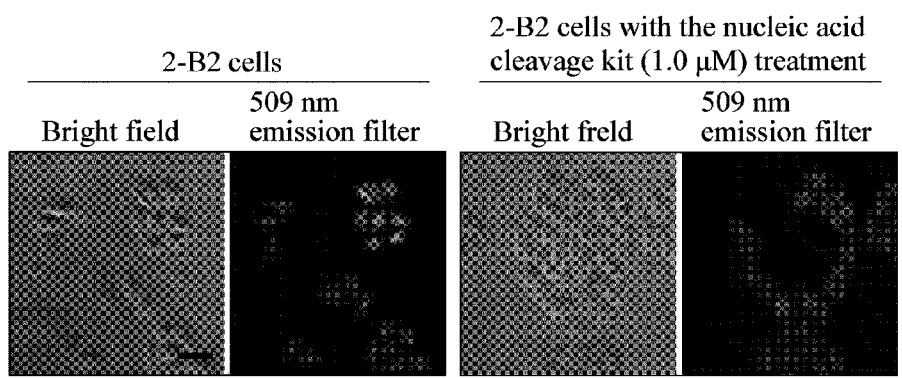
FIG. 11a is a microscopic image of the 2-B2 cells after the treatment of the nucleic acid cleavage kit in accordance with the first embodiment of the present invention.

FIG. 11 shows the level of EGFP expression of 2-B2 cells treated with the nucleic acid cleavage kit under microscopy. The 2-B2 cells were respectively photographed in bright field and with a 509 nm emission filter, which can absorb all sorts of light except green fluorescence. As shown in FIG. 11a, the green fluorescence signal of the 2-B2 cells treated with the nucleic acid cleavage kit is weaker than one without the treatment. It is due to the cleavage reaction performed by the nucleic acid cleavage kit to reduce the expression level of EGFP.

Meanwhile, the genomic DNA PCR technique was used to examine the in vivo cleavage reaction with high sequence specificity generated by the nucleic acid cleavage kit. Total genomic DNAs of the 2-B2 cells with or without the nucleic acid cleavage kit treatment were isolated by Genomic DNA mini kit (Geneaid, GB100). General standard reagents were used for all genomic DNA PCR reactions. Two sets of primers were used herein. The first set was primers for sequencing part of EGFP expression sequence for (the part of the sequence expressing EGFP) (5'-CCTACGGCGTGCAGT-GCTTCAGC-3' (SEQ ID NO:1 in FIG. 15) and 5'-CGGC-GAGCTGCACGCTGCCGTCCTC-3' (SEQ ID NO:2 in FIG. 15), also called as E primers in the following). The second set was primers for sequencing the oligonucleotide recognition sequence (5'-TACCGGACTCAGATCTC-GAGCTCA-3' (SEQ ID NO:3 in FIG. 15), also called as T primers in the following).

The PCR cycle program initiated at 95° C. for 5', followed by 30 cycles of 95° C. for 45", 60° C. for 30", 72° C. for 45", and finally at 72° C. for 5'. Amplified PCR products were electrophoresed on 2% agarose gels and visualized by using UV fluorescence.

Figure 11B:
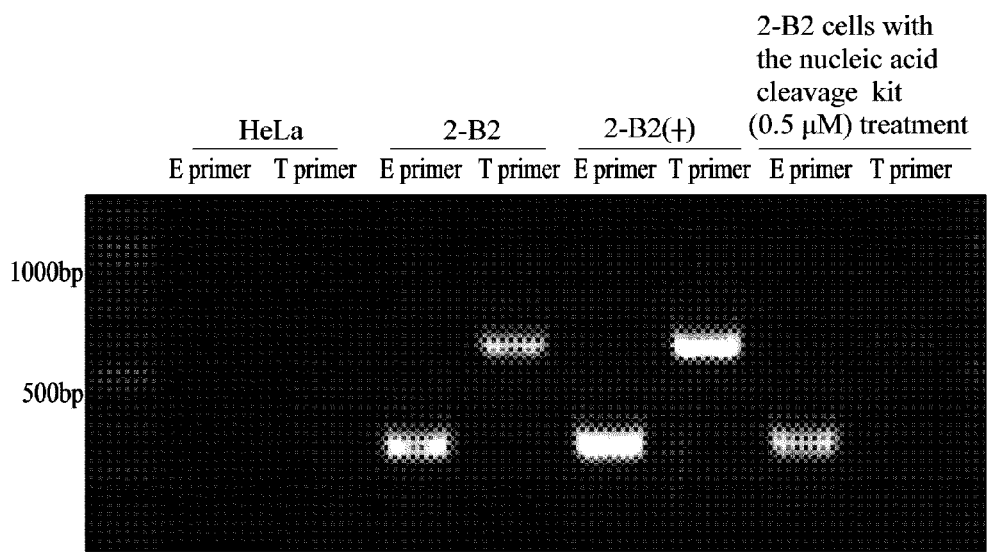
FIG. 11b is an electrophoregram of the genomic DNA PCR products in accordance with the first embodiment of the present invention.
Figure 11C:
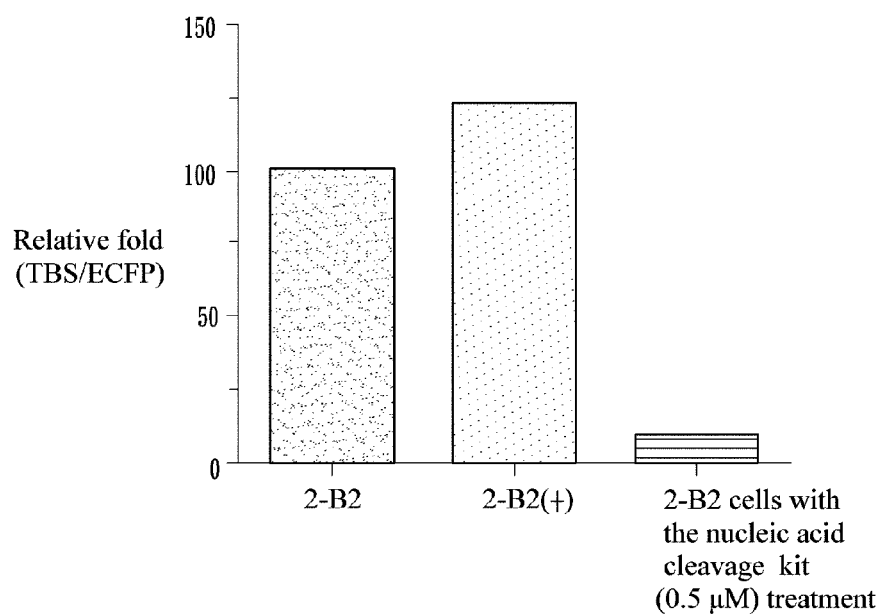
FIG. 11c is a bar diagram illustrating the signal strength of the products shown in FIG. 11b.

As shown in FIG. 11b, comparing to the amount of the T-primer induced products from 2-B2 cells processed without the nucleic acid cleavage kit treatment (marked with "2-B2" in FIG. 11b) and the products processed with the light exposure but no nucleic acid cleavage kit treatment (marked with "2-B2(+)" in FIG. 11b), the products with the nucleic acid cleavage kit treatment were at extremely low expression and thereby it indicated that the 2-B2 cells processed with the nucleic acid cleavage kit cannot synthesize the products containing the T primer sequence after genomic DNA PCR. The genomic DNA PCR products containing the E primers were used for the control groups. FIG. 11c is a bar diagram showing the electrophoresis result obtained in FIG. 11b in accordance with the signal strength of the products and the data of the 2-B2 cells without any processing was used for standardization.

Figure 12:
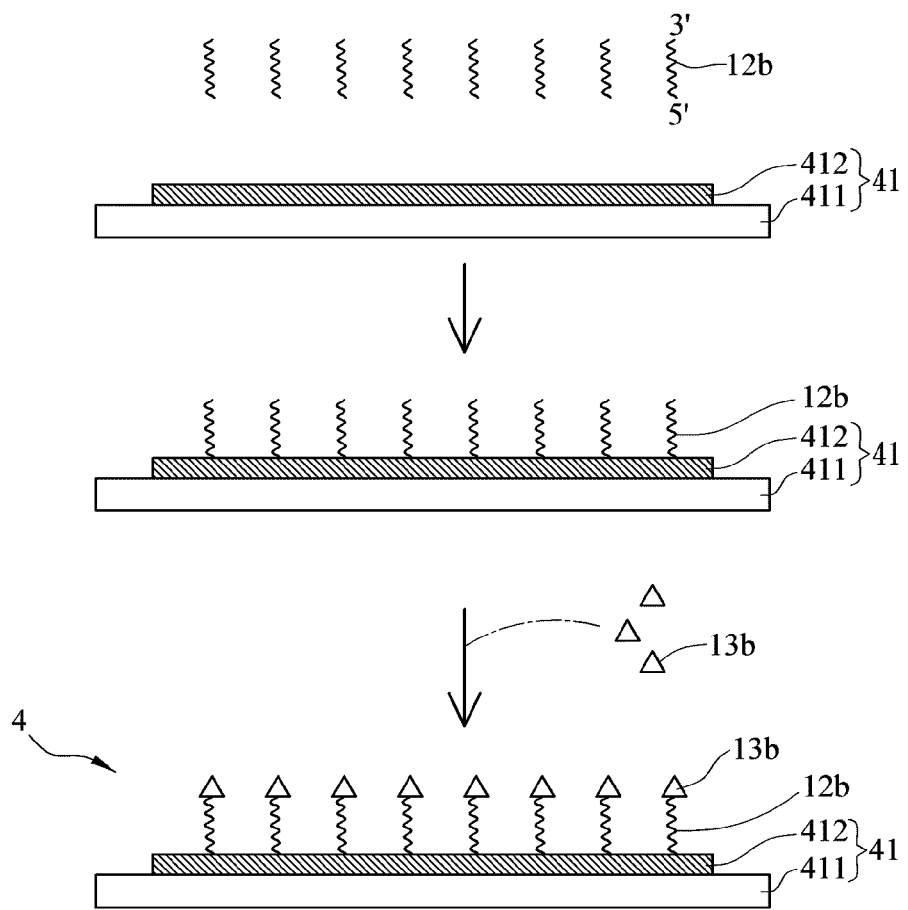
FIG. 12 is a synthesis flow chart of the nucleic acid cleavage kit in accordance with the third embodiment of the present invention.

Experiment 3: The Manufacture of the Nucleic Acid Cleavage Kit in Accordance with the Second Embodiment As shown in FIG. 12, the carrier 41 was generated by coating the bonding layer 412 on the base 411. The base 411 is a flat substrate. The bonding layer 412 was synthesized via reduction of gold salt by sodium citrate, and then disposed on the base 411 to form the carrier 41 by coating (please reference to Frens, G. Controlled nucleation for the regulation of the particle size in monodisperse gold suspensions, Nat. Phys. Sci., 241, 20-22, 1973, and Grabar, et al., Preparation and characterization of Au colloid monolayers., Anal. Chem., 67, 735-743, 1995).

Then, the oligonucleotides 12b were connected to the bonding layer 412, and the connection method can refer to the connection method between the oligonucleotides 12a and the carrier 11 described in the first experiment such that the detailed description thereof can be omitted. The method of connecting the nucleic acid cleavage reagent 13b to the oligonucleotide 12b can also be refer to the first experiment such that the detailed description thereof can be omitted.

Experiment 4: The Cleavage with High Sequence Specificity of the Nucleic Acid Cleavage Kit in Accordance with the Fourth Embodiment In the present experiment, the target nucleic acid was the pGEM-T easy plasmid (Promega, Madison, Wis., USA) containing the oligonucleotide recognition sequence 100 ng (nanogram), and the control group was pGEM-T easy plasmid without the oligonucleotide recognition sequence 100 ng. Both of the target nucleic acids and the control group have been created a Nae I site, and then were cleaved by restriction enzyme cleavage technique to form linear plasmid nucleic acids with its original length respectively. In more detailed, the Nae I site were located at 2,710 in both of the target nucleic acids and the control group.

Then, each of the target nucleic acids and the control group separately mixed with the nucleic acid cleavage kit in Tris-base buffer at 37° C. for 72 hrs. The molar ratio of the target nucleic acids/control group to the oligonucleotide is 1:1. Because the nucleic acid cleavage agents in the present experiment were hydrazone compounds, the reactions were sequentially exposed to 302 nm ultraviolet light for 30 mins for activation of the cleavage. In more detailed, the source of the 302 nm ultraviolet light is an F8T5 UV-B lamp (16-watt, peak wavelength at 302 nm).

The products derived from the target nucleic acids and the control group were purified after cleavage respectively, and then the purified products were separated in a 2.0% agarose gel and visualized by using an imaging system (BioSpectrum AC [formerly AC1 AutoChemi]; UVP, Inc., Upland, Calif., USA). Furthermore, the 2689-bps DNA fragment bands derived from the target nucleic acids after cleavage were then isolated and sequenced (ABI Prism 3730 DNA Sequencer; AME Bioscience A/S, Toroed, Norway).

Figure 13A:
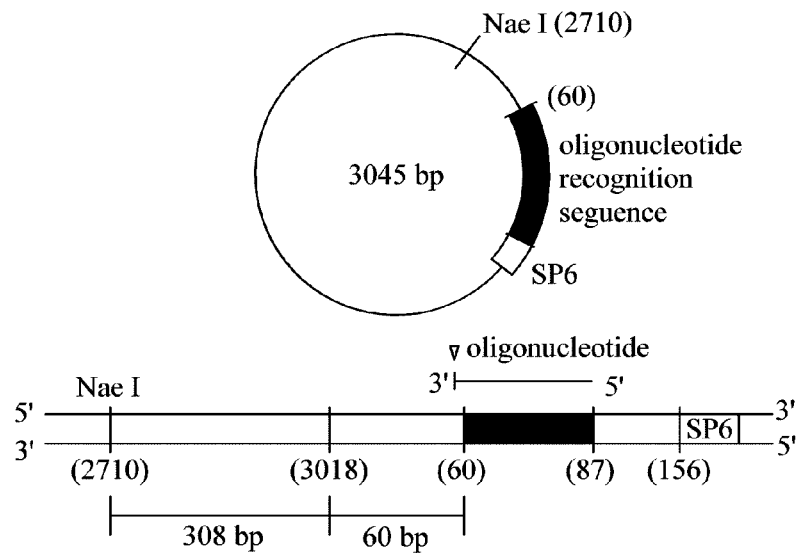
FIG. 13a is a schematic diagram showing the target nucleic acid and the useful sites thereof in accordance with the second experiment of the present invention.
Figure 13B:
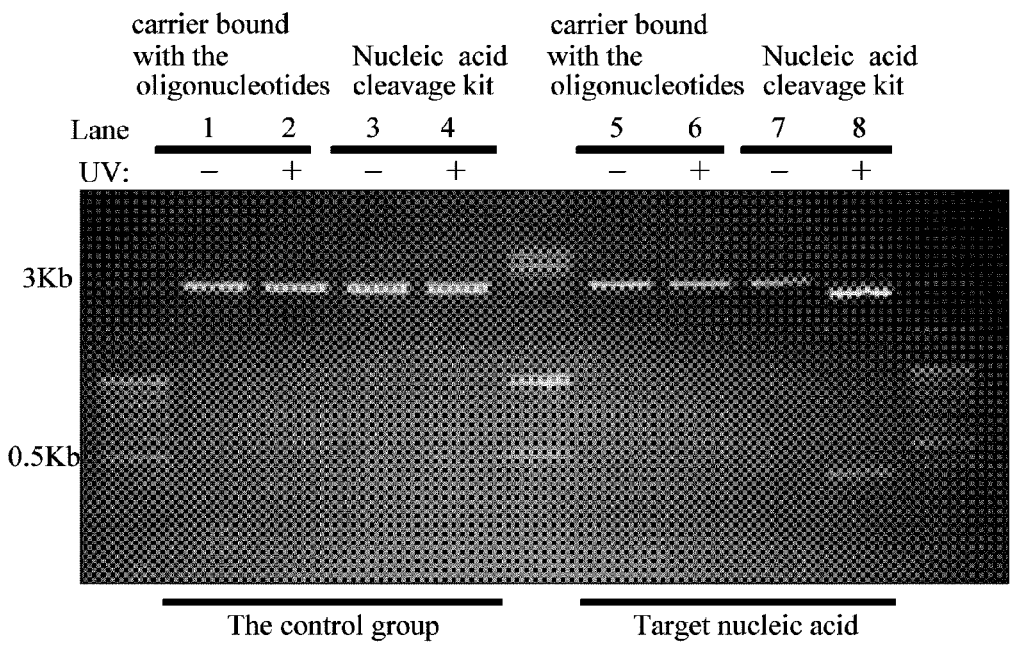
FIG. 13b is an electrophoregram of the target nucleic acids respectively cleaved by the restriction enzymes and nucleic acid cleavage kit in accordance with the fourth experiment of the present invention.

As shown in FIG. 13a, the target nucleic acids and the control group have been respectively cleaved by Nae I restriction enzyme to form linear plasmid nucleic acids previously, and then interacted with the nucleic acid cleavage kit. The oligonucleotides included in the nucleic acid cleavage kit can recognize the at least partial sequence of the target nucleic acid with high specificity such that each of the oligonucleotides bound to the at least partial sequence of the target nucleic acid to form a triple helix structure (60-87). After photoactivation induced by the ultraviolet light, the nucleic acid cleavage agents were able to cleave downstream of the 3' end of the triple helix and thereby cleaved each of the complete linear plasmid nucleic acids into two fragments. As lane 8 shown in FIG. 13, the larger one is about 2,689-bps in length, and the smaller one is about 356-bps in length. In contrast, the control group was observed with the length of original 3,045 bps (as indicated in lane 4) because it is without the oligonucleotide recognition sequence.

Figure 14:
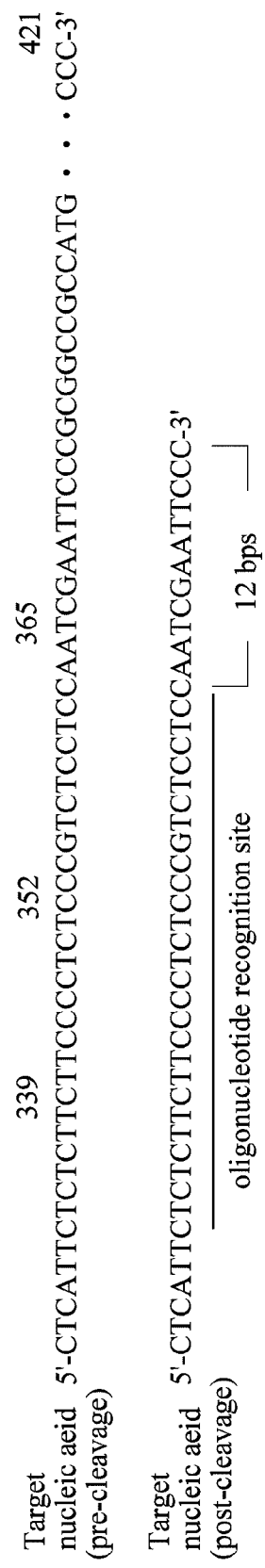
FIG. 14 is a diagram illustrating the auto-sequencing result adjacent to the triple helix on the target nucleic acid in accordance with the fourth experiment of the present invention.

Primers were designed based on the 311 bps downstream from the oligonucleotide recognition sequence of the plasmids so that primers can be used for auto-sequencing of the target nucleic acids treated with the target nucleic acid cleavage kit (ABI Prism 3730 DNA sequencer; AME Bioscience A/S, Toroed, Norway). The primer sequence is 5'-AGC-GAGTCAGTGAGCGAGGA-3' (SEQ ID NO:4 in FIG. 15) in this experiment. As shown in FIG. 14, comparing the auto-sequencing result with the original sequence of the target nucleic acid before the treatment of the nucleic acid cleavage kit, each of the post-cleavage sequences was truncated 12 bps downstream from the 3' end of the triple helix (374) at which the auto-sequencing process stopped. It indicated that certain position was one of the ends of the target nucleic acid after the cleavage of generated by the nucleic acid cleavage kit. It further confirmed that the nucleic acid cleavage kit of the present invention can perform a cleavage reaction with high sequence specificity.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. A nucleic acid cleavage kit functioning on a target nucleic acid, comprising:
    a carrier;
    an oligonucleotide, wherein a first end of the oligonucleotide is bonded with the carrier to recognize at least partial sequence of the target nucleic acid; and
    a nucleic acid cleavage agent bonded to a second end of the oligonucleotide to cleave the target nucleic acid,
    wherein the carrier comprises a base and a plurality of bonding layers, the base comprises a first surface, the first surface comprises a plurality of protrusions defining a plurality of wells, each of the bonding layers is disposed on the first surface of the base in one of the wells, and the first end of the oligonucleotide is bound to the bonding layer of the carrier.

* * * * *

SEQUENCE LISTING

<160> NUMBER OF SEQ ID NOS: 4

<210> SEQ ID NO 1
<211> LENGTH: 23
<212> TYPE: DNA
<213> ORGANISM: Artificial sequence
<220> FEATURE:
<223> OTHER INFORMATION: Synthetic primer

<400> SEQUENCE: 1
cctacggcgt gcagtgcttc agc                                             23

<210> SEQ ID NO 2
<211> LENGTH: 25
<212> TYPE: DNA
<213> ORGANISM: Artificial sequence
<220> FEATURE:
<223> OTHER INFORMATION: Synthetic primer

<400> SEQUENCE: 2
cggcgagctg cacgctgccg tcctc                                           25

<210> SEQ ID NO 3
<211> LENGTH: 24
<212> TYPE: DNA
<213> ORGANISM: Artificial sequence
<220> FEATURE:
<223> OTHER INFORMATION: Synthetic primer

<400> SEQUENCE: 3
taccggactc agatctcgag ctca                                            24

<210> SEQ ID NO 4
<211> LENGTH: 20

```
<212> TYPE: DNA
<213> ORGANISM: Artificial sequence
<220> FEATURE:
<223> OTHER INFORMATION: Synthetic primer

<400> SEQUENCE: 4
agcgagtcag tgagcgagga                                             20
```